US007795451B2

(12) United States Patent
Chavhan et al.

(10) Patent No.: US 7,795,451 B2
(45) Date of Patent: Sep. 14, 2010

(54) POLYMORPHIC FORMS OF FLUVASTATIN SODIUM AND PROCESS FOR PREPARING THE SAME

(75) Inventors: Bhausaheb Chavhan, Uttar Pradesh (IN); Arun Kumar Awasthi, Uttar Pradesh (IN); Richa Aggarwal, Uttar Pradesh (IN); Rani S. Beena, Uttar Pradesh (IN); Soumendu Paul, Uttar Pradesh (IN); Rajesh Kumar Thaper, Uttar Pradesh (IN); Sushil Kumar Dubey, Uttar Pradesh (IN)

(73) Assignee: Jubilant Organosys Limited, Noida (IN)

( * ) Notice: Subject to any disclaimer, the term of this patent is extended or adjusted under 35 U.S.C. 154(b) by 155 days.

(21) Appl. No.: 11/815,969

(22) PCT Filed: Feb. 10, 2006

(86) PCT No.: PCT/IN2006/000045

§ 371 (c)(1),
(2), (4) Date: Jan. 3, 2008

(87) PCT Pub. No.: WO2006/085338

PCT Pub. Date: Aug. 17, 2006

(65) Prior Publication Data

US 2008/0207919 A1    Aug. 28, 2008

(30) Foreign Application Priority Data

Feb. 11, 2005   (IN) .......................... 302/DEL/2005

(51) Int. Cl.
*C07D 209/12*   (2006.01)
(52) U.S. Cl. ..................................... 548/494
(58) Field of Classification Search ................... 548/494
See application file for complete search history.

(56) References Cited

U.S. PATENT DOCUMENTS

| 4,739,073 | A |   | 4/1988  | Kathawala |
|-----------|---|---|---------|-----------|
| 6,124,340 | A |   | 9/2000  | Horvath |
| 6,696,479 | B2 |  | 2/2004  | Van Der Schaaf et al. |
| 6,743,926 | B2 | * | 6/2004  | Wolleb et al. ............... 548/494 |
| 6,858,643 | B2 | * | 2/2005  | Van Der Schaaf et al. ... 514/419 |
| 7,432,380 | B2 | * | 10/2008 | Van Der Schaaf et al. ... 548/494 |
| 2005/0032884 | A1 | | 2/2005 | Lifshitz-Liron et al. |
| 2005/0038114 | A1 | | 2/2005 | Lifshitz-Liron et al. |
| 2005/0119342 | A1 | | 6/2005 | Frenkel |

FOREIGN PATENT DOCUMENTS

| WO | WO/2004/096765 | 11/2004 |
| WO | WO/2005/080332 | 9/2005  |

* cited by examiner

*Primary Examiner*—Rei-tsang Shiao
(74) *Attorney, Agent, or Firm*—Workman Nydegger

(57) ABSTRACT

Disclosed herein are novel polymorphic forms of Fluvastatin sodium, wherein said polymorphic forms are designated as $J_F$, $J_{F1}$, $J_{F2}$, $J_{F3}$ and are characterized by their powder X-ray diffraction patterns, Infrared absorption spectrums, thermo gravimetric analysis and differential scanning calorimetry. The processes for preparing said polymorphic forms are also disclosed. The present invention also relates to process for preparing amorphous form of Fluvastatin sodium.

20 Claims, 17 Drawing Sheets

POLYMORPHIC FORMS OF FLUVASTATIN SODIUM AND PROCESS FOR PREPARING THE SAME

FIELD OF THE INVENTION

Figure 1:
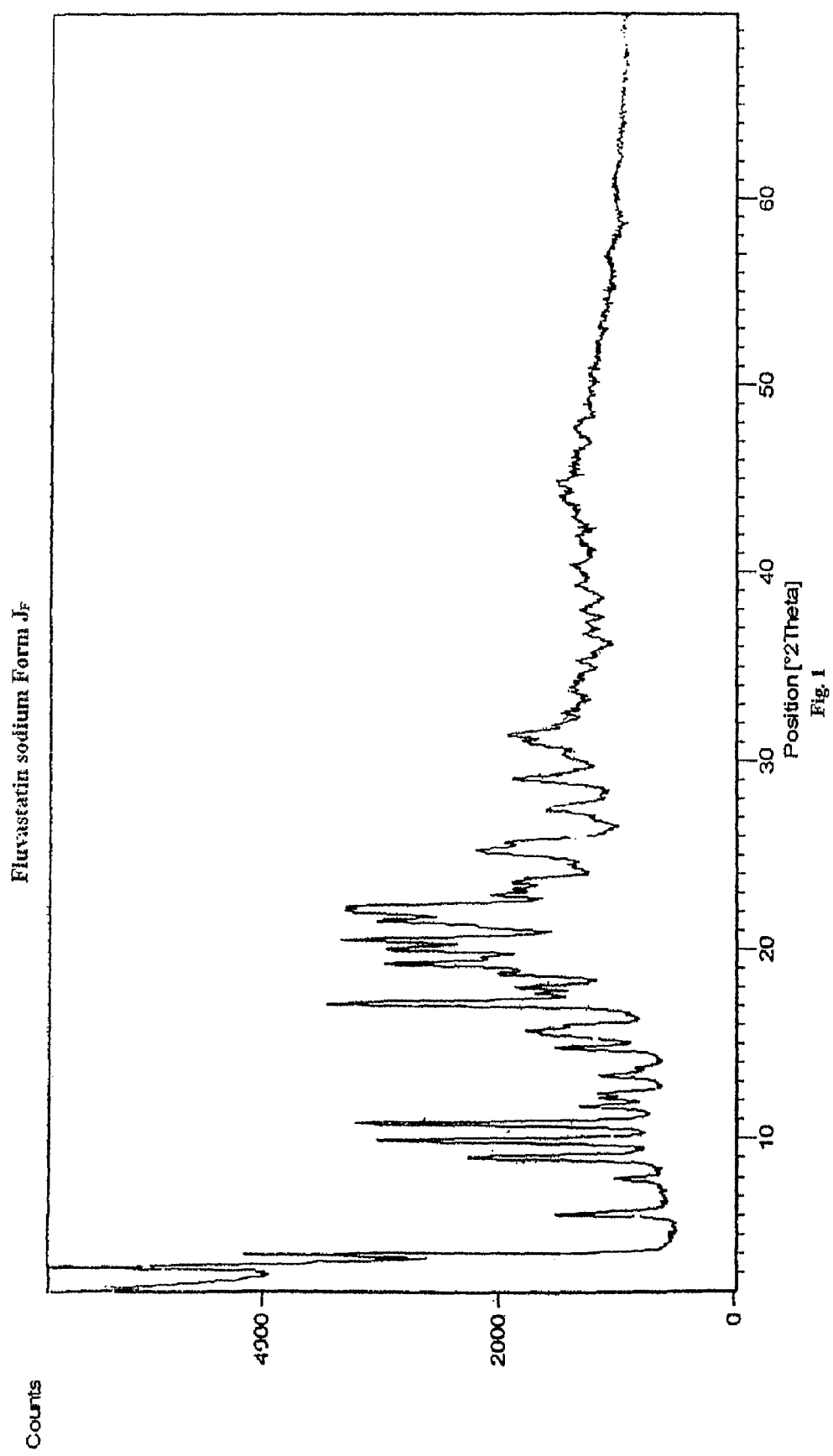

This invention, in general relates to the field of HMG-CoA Reductase inhibitors, in particular to the field of Fluvastatin sodium. More specifically the present invention provides novel crystalline polymorphic forms of Fluvastatin sodium, process for preparing the same. Also the present invention provides a process for preparation of amorphous Fluvastatin sodium.

BACKGROUND OF THE INVENTION

Fluvastatin sodium is known by its chemical name (±)-7-(3-(4-fluorophenyl)-1-(1-methylethyl)-1H-indol-2-yl)-3,5-dihydroxy-6-heptenoic acid monosodium salt. Fluvastatin sodium is a racemic mixture of the 3R, 5S- and 3S, 5R-dihydroxy enantiomers represented by the Formula I.

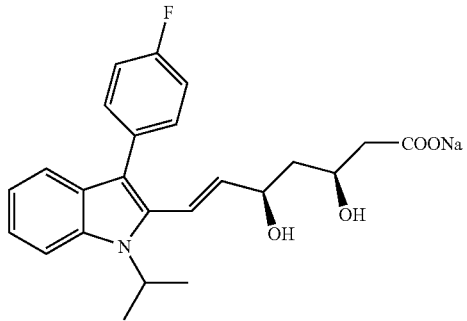

Formula I

Fluvastatin sodium is a competitive inhibitor of HMG-CoA reductase, which is responsible for the conversion of 3-hydroxy-3-methylglutaryl-coenzyme A (HMG-CoA) to mevalonate, a precursor of sterols, including cholesterol. The inhibition of cholesterol biosynthesis reduces the cholesterol in hepatic cells, which stimulates the synthesis of LDL receptors and thereby increases the uptake of LDL particles. The end result of these biochemical processes is a reduction of the plasma cholesterol concentration.

Fluvastatin as well as its sodium salt are described in U.S. Pat. No. 4,739,073. In this patent Fluvastatin sodium is obtained by lyophilization and discloses the amorphous form, which is unsuitable for large-scale production as disclosed in the further literature.

U.S. Pat. No. 6,124,340, describes that lyophilization of Fluvastatin sodium as was performed in examples 6(b) and 8 of '073 patent yields a mixture of a crystalline form, designated as Form A and amorphous material. The estimated amount of Form A obtained by lyophilization as described by '340 patent is about 50% in the said mixture.

The '340 patent describes a new crystalline form designated as Form B. The crystalline Form B is obtained either by transformation of material containing Form A in a slurry of a mixture of an organic solvent and water, or by crystallization from an organic solvent and water mixture. This patent also describes that Form B is less hygroscopic than Form A or the amorphous form of the Fluvastatin sodium, which improves handling and storage of the compound.

U.S. Pat. No. 6,696,479 describes crystalline forms of Fluvastatin sodium hydrates designated as form C, D, E, and F. The water content of the forms ranges between 3 to 32%. The patent also describes a new process for the preparation of highly crystalline form of Fluvastatin sodium Form A. The new crystal forms of Fluvastatin sodium were obtained by storing the sample under atmosphere ranging between 20 and 90% relative humidity.

International Publication No. WO2004/096765A2 describes crystalline form of Fluvastatin sodium monohydrate depicted as BA. The water content ranges from 3 to 6%. Similarly International Publication No. WO2005/080332 discloses novel crystalline form of Fluvastatin sodium with characteristic PXRD peaks. The water content ranges from 1 to 8%.

U.S. Patent Application No. 2005032884, U.S. Patent Application No. 20050038114 and U.S. Patent Application No. US2005119342 disclose novel crystalline forms of Fluvastatin sodium, some of which are hydrates and solvates.

Objective of the present invention is to provide novel and stable polymorphic forms of Fluvastain sodium, which can effectively used for different pharmaceutical formulation. Further, the process for preparing said polymorphic forms is cost efficient and the produced polymorph is easy to handle and convenient to operate on commercial scale.

Further and other objects of the invention will be realized by those skilled in the art from the following summary of the invention and detailed description of examples thereof.

SUMMARY OF THE INVENTION

In accordance with principal embodiment of the present invention, there are provided novel crystalline polymorphic forms of Fluvastain sodium, wherein said polymorphic forms are designated as $J_F$, $J_{F1}$, $J_{F2}$, $J_{F3}$ and are characterized by using analytical tools selected from infrared absorption spectrum, X-ray powder diffraction pattern, thermo gravimetric analysis (TGA), differential scanning calorimetry (DSC). Further the present invention also provides a process for the preparation of amorphous form of Fluvastatin sodium.

In accordance with another embodiment, the present invention provides a crystalline polymorphic form of Fluvastatin sodium, wherein said polymorphic form is designated as $J_F$ characterized by a PXRD pattern having peaks at 3.3, 3.9, 10.0, 10.9, 17.1, 19.3, 20.6±0.2°2θ, essentially as represented in FIG. 1.

Figure 2:
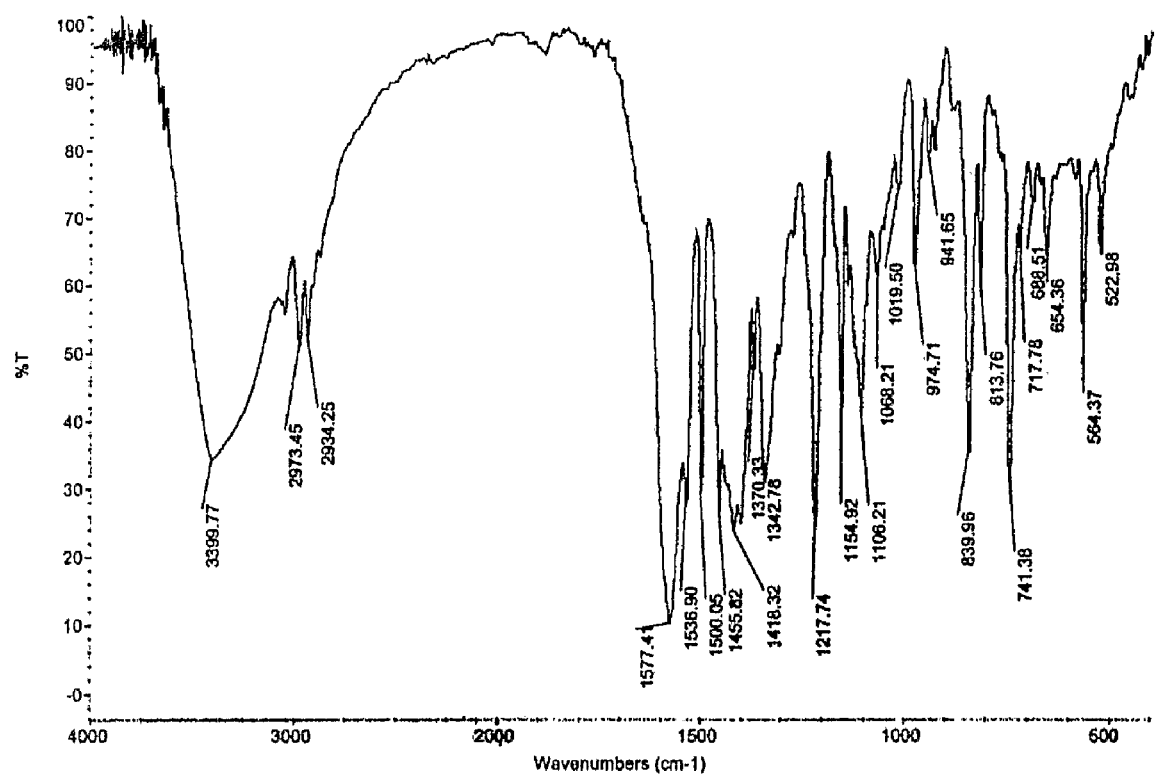

In accordance with another embodiment, the present invention provides a crystalline polymorphic form of Fluvastatin sodium, wherein said polymorphic form is designated as $J_F$, characterized by having an infrared spectrum in KBr comprising one or more characteristic peaks selected from absorption bands (cm$^{-1}$) at 3399, 1577, 1500, 1217, 1154, 1106, 839, 741, 564 essentially as represented in FIG. 2.

Further embodiment of the present invention provides a process for preparing said polymorphic form $J_F$, wherein the process comprises of dissolving Fluvastatin lower alkyl ester in methanol, adding sodium hydroxide to the solution and then isolating Fluvastatin sodium Form $J_F$ from the solution by adding anti-solvent selected from lower alkyl alcohols.

In accordance with another embodiment, the polymorphic form $J_F$ is prepared by dissolving Fluvastatin sodium in methanol, followed by addition of anti-solvent selected from lower alkyl alcohols.

Figure 5:
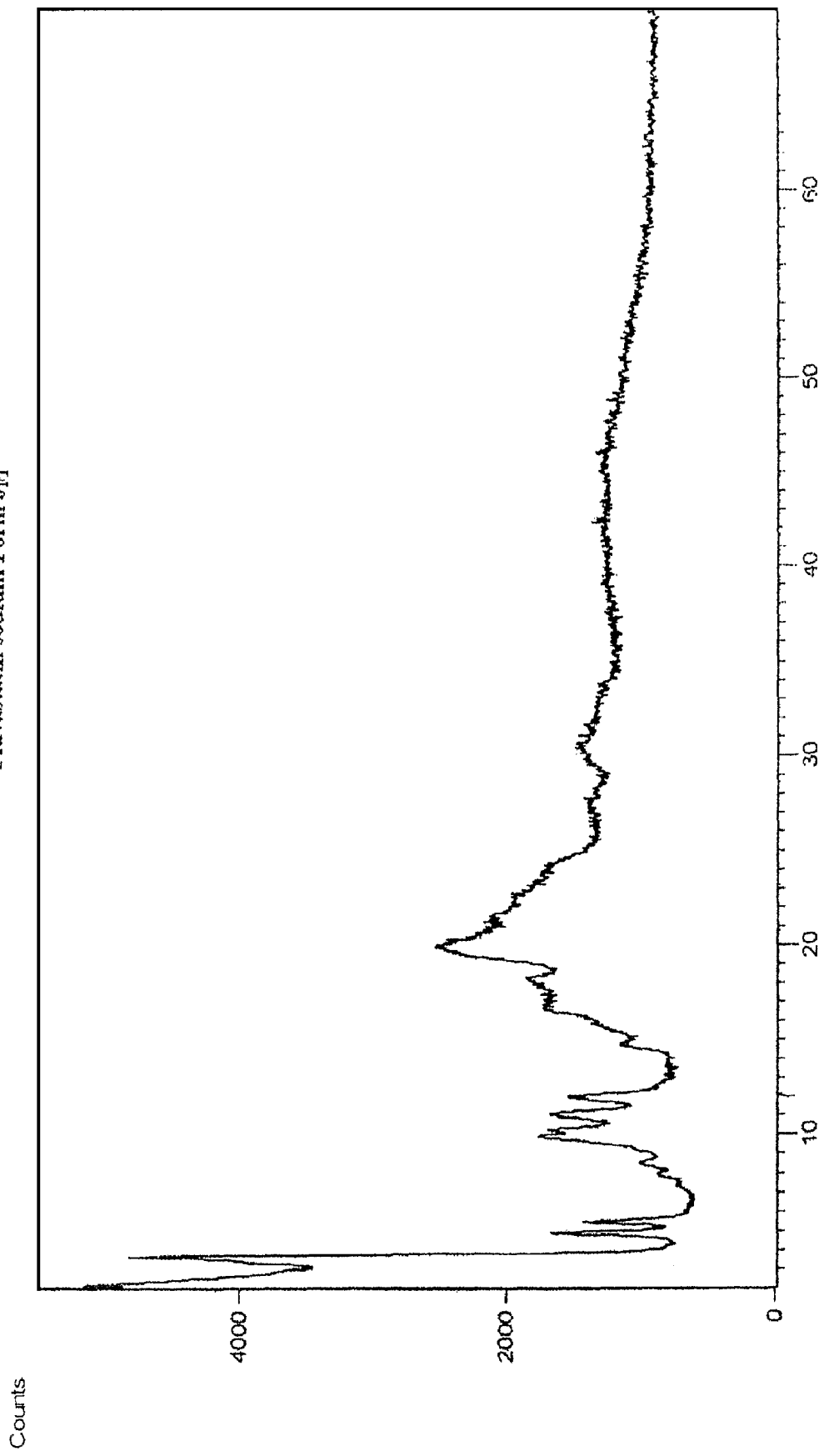

In accordance with yet another embodiment of present invention there is provided a novel crystalline polymorphic form of Fluvastatin sodium, wherein said polymorphic form is designated as $J_{F1}$, characterized by a PXRD pattern with peaks at 3.7, 4.9, 5.5, 9.8, 10.2, 11.2, 12.1±0.2°2θ, essentially as represented in FIG. 5.

Figure 6:
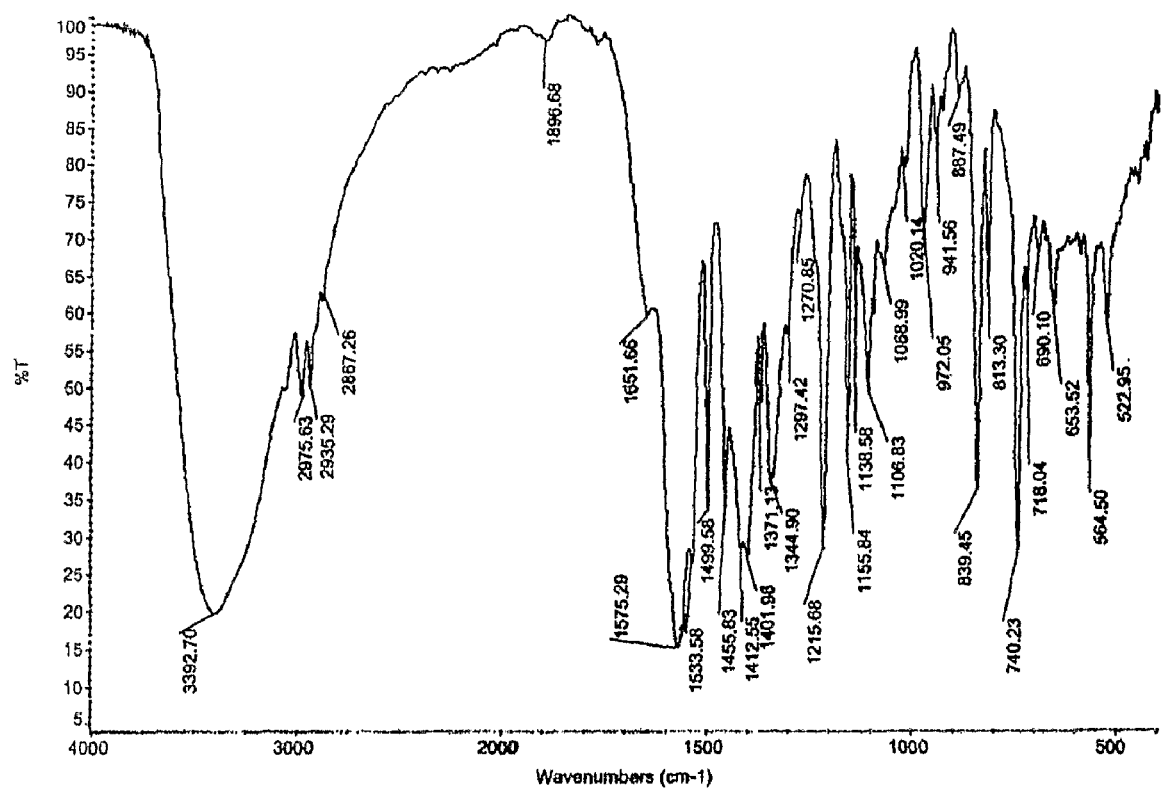

In accordance with yet another embodiment of present invention there is provided a novel crystalline polymorphic form of Fluvastatin sodium, wherein said polymorphic form is designated as $J_{F1}$, characterized by having an infrared spectrum in KBr comprising one or more characteristic peaks selected from absorption bands ($cm^{-1}$) at 3392, 1575, 1215, 1155, 839, 813, 740, 564, essentially as represented in FIG. 6.

Further embodiment of the present invention provides a process for preparing said polymorphic form $J_{F1}$, wherein the process comprises of dissolving Fluvastatin lower alkyl ester in methanol, adding sodium hydroxide to the solution and then isolating Fluvastatin sodium Form $J_{F1}$ from the solution by adding anti-solvent selected from nitriles.

In accordance with another embodiment, the polymorphic form $J_{F1}$ can be prepared by dissolving Fluvastatin sodium in methanol, followed by addition of anti-solvent selected from nitriles.

Figure 9:
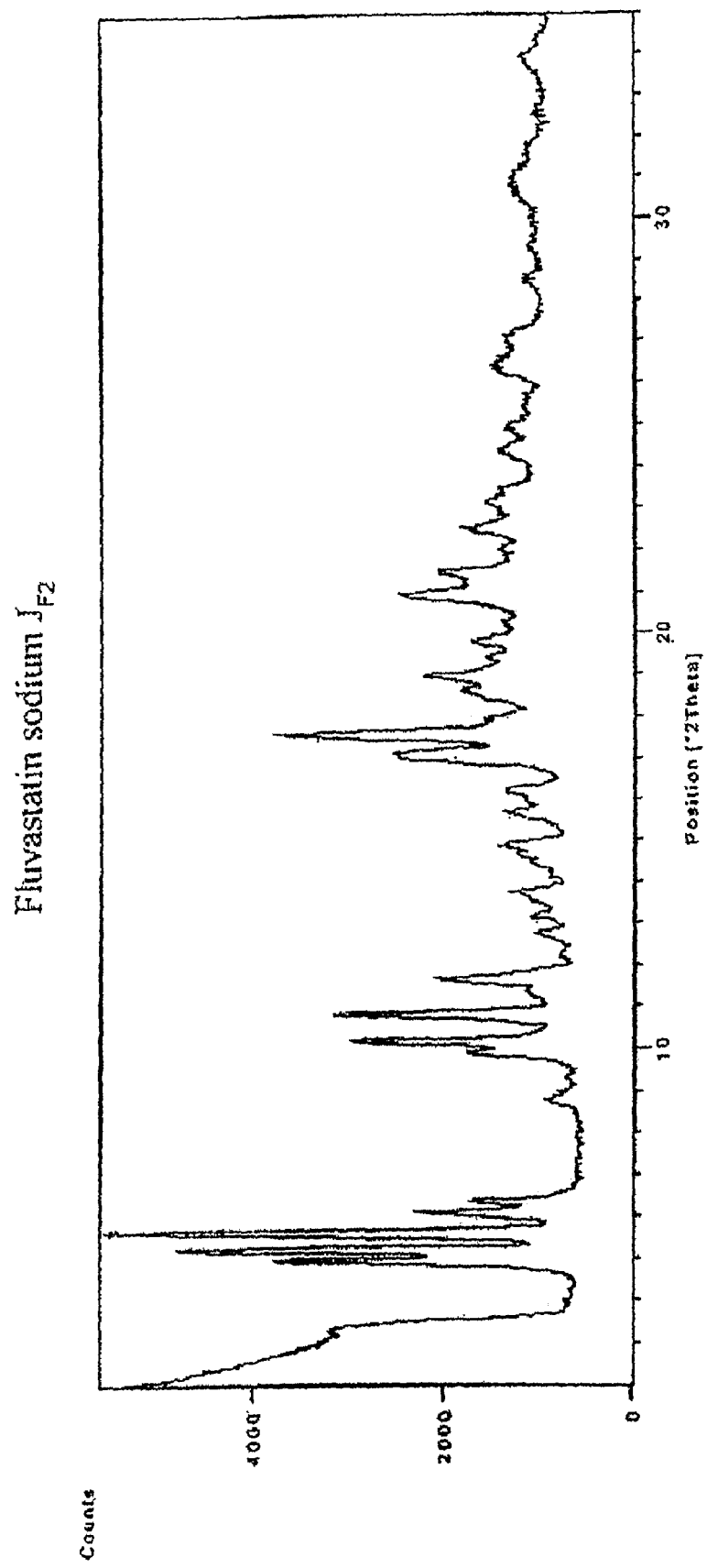

In accordance with yet another embodiment of present invention there is provided a novel crystalline polymorphic form of Fluvastatin sodium, wherein said polymorphic form is designated as $J_{F2}$, characterized by a PXRD pattern with peaks at 4.9, 5.2, 5.6, 17.6±0.2°2θ, essentially as represented in FIG. 9.

Figure 10:
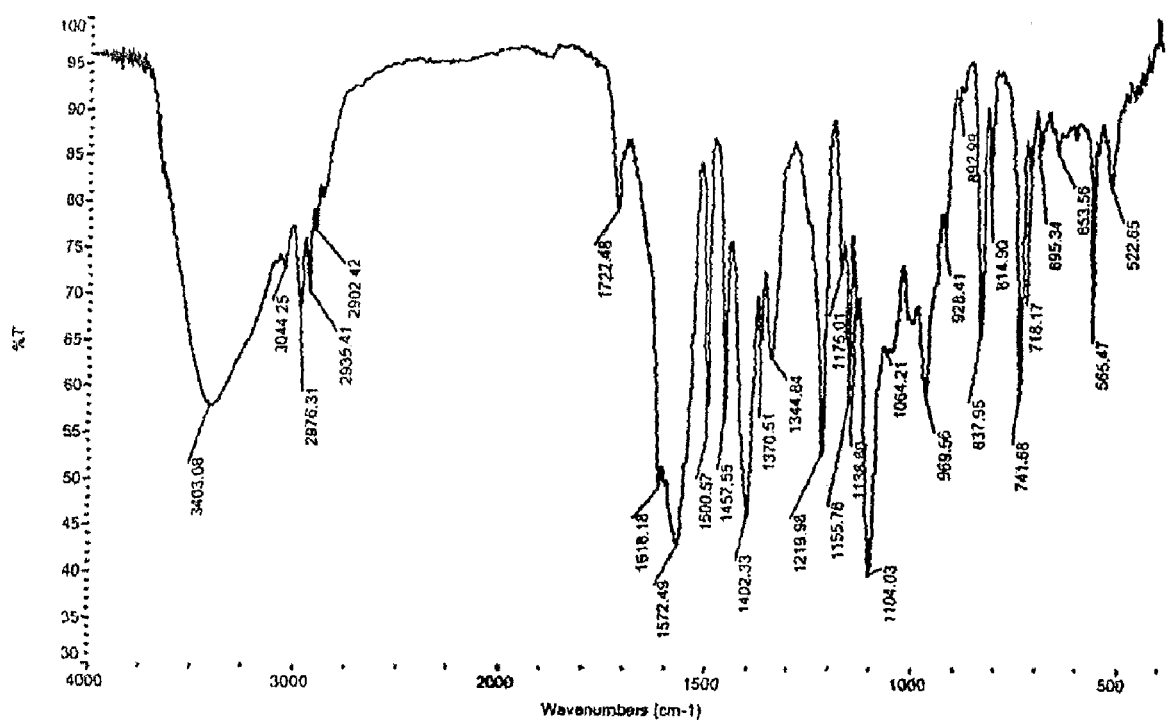

In accordance with yet another embodiment of present invention there is provided a novel crystalline polymorphic form of Fluvastatin sodium, wherein said polymorphic form is designated as $J_{F2}$, characterized by having an infrared spectrum in KBr comprising one or more characteristic peaks selected from absorption bands ($cm^{-1}$) at 3403, 1722, 1572, 1500, 1457, 1402, 1219, 1104, 969 essentially as represented in FIG. 10.

Further embodiment of the present invention provides a process for preparing said polymorphic form $J_{F2}$, wherein the process comprises of dissolving Fluvastatin lower alkyl ester in methanol, adding sodium hydroxide to the solution and then isolating Fluvastatin sodium Form $J_{F2}$ from the solution by adding anti-solvent selected from alkyl esters followed by air-drying.

In accordance with another embodiment, the polymorphic form $J_{F2}$ is prepared by dissolving Fluvastatin sodium in methanol, followed by addition of anti-solvent selected from alkyl esters followed by air-drying.

Figure 13:
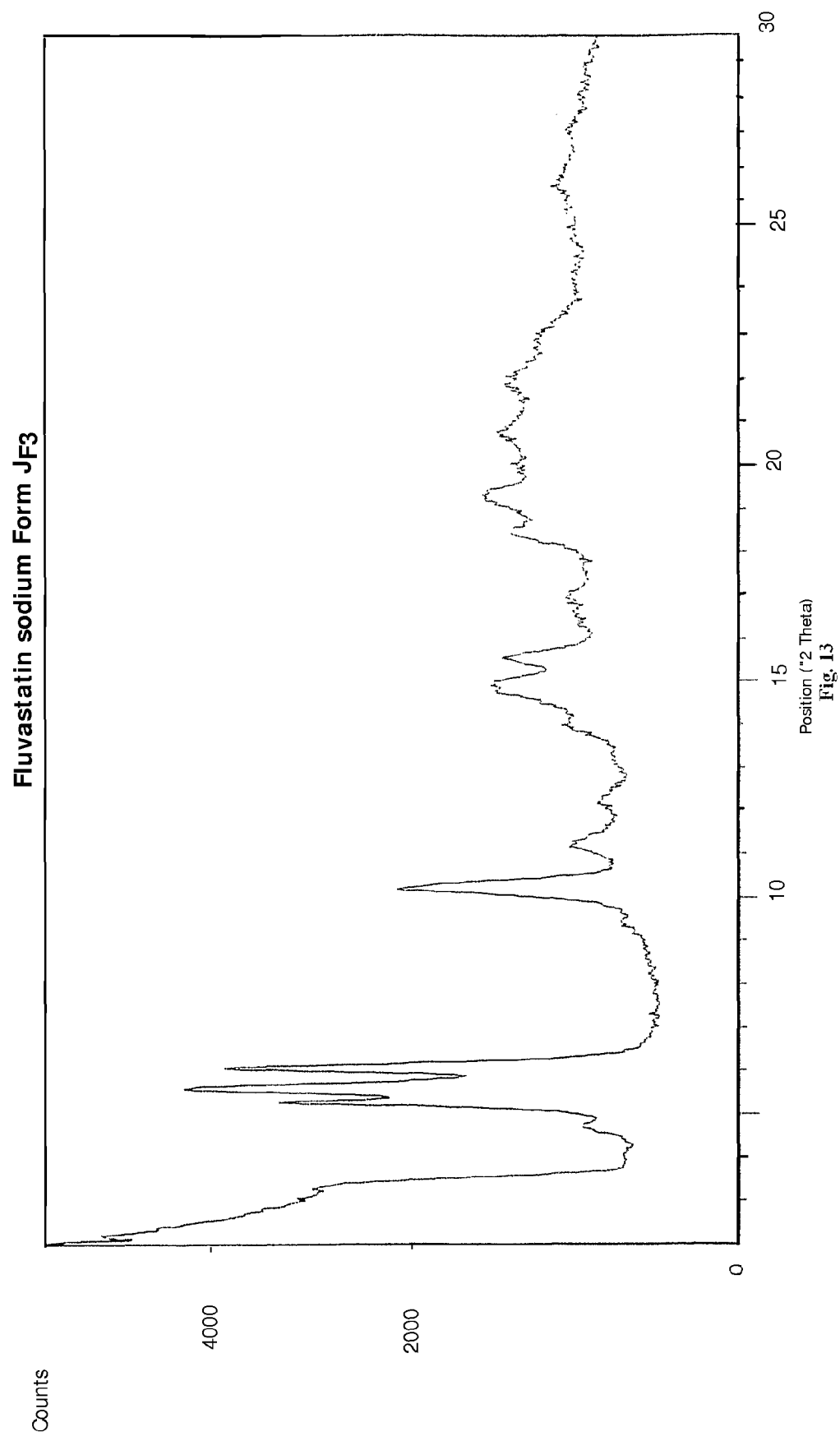

In accordance with yet another embodiment of present invention there is provided a novel crystalline polymorphic form of Fluvastatin sodium, wherein said polymorphic form is designated as $J_{F3}$ characterized by a PXRD pattern with peaks at 5.2, 5.5, 6.0±0.2°2θ, essentially as represented in FIG. 13.

Figure 14:
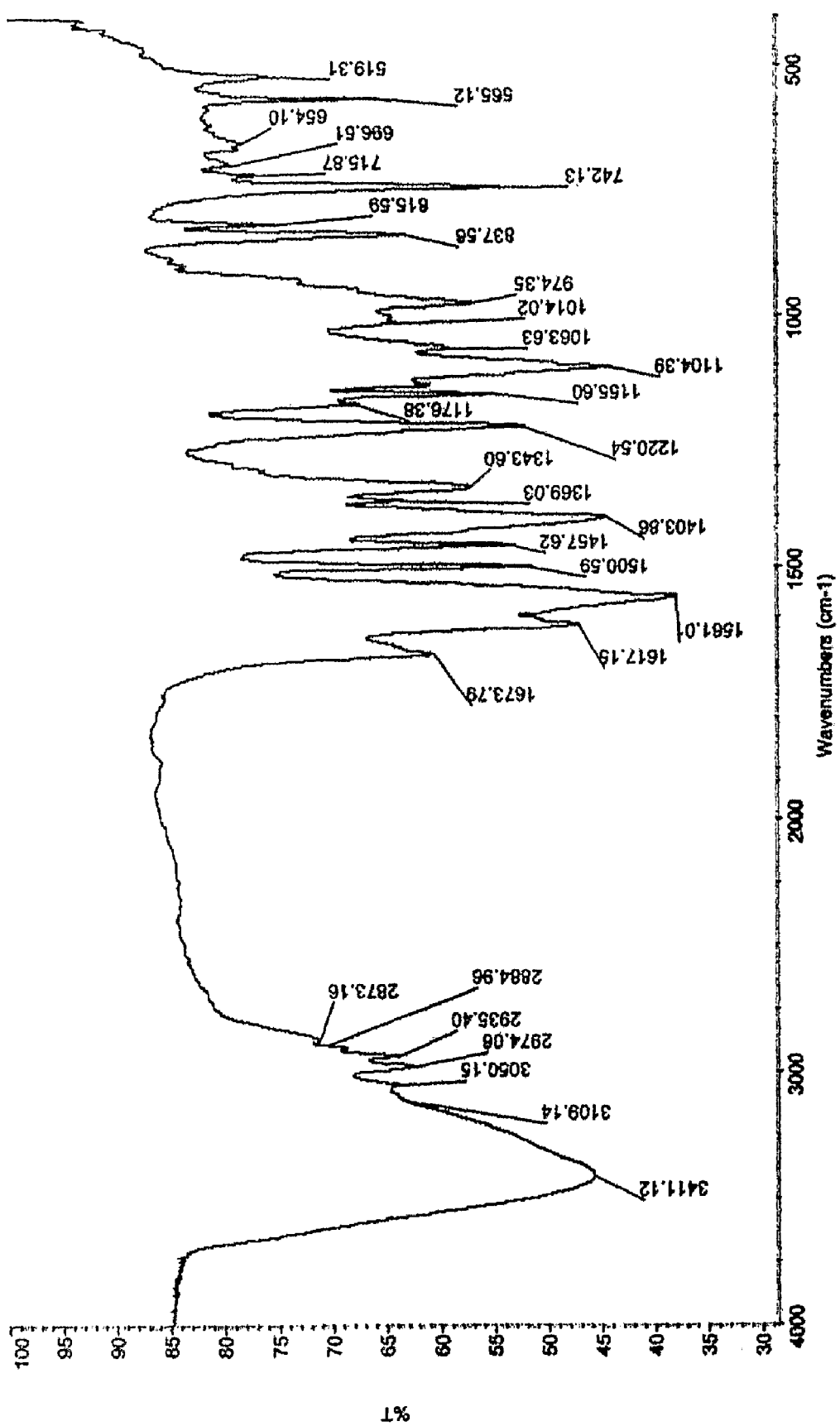

In accordance with yet another embodiment of present invention there is provided a novel crystalline polymorphic form of Fluvastatin sodium, wherein said polymorphic form is designated as $J_{F3}$ characterized by having an infrared spectrum in KBr comprising one or more characteristic peaks selected from absorption bands ($cm^{-1}$) at 3411, 1561, 1500, 1457, 1403, 1220, 1104, 837, 742, 565 essentially as represented in FIG. 14.

Further embodiment of the present invention provides a process for preparing said polymorphic form $J_{F3}$ wherein the process comprises of dissolving Fluvastatin lower alkyl ester in methanol, adding sodium hydroxide to the solution and then isolating Fluvastatin sodium Form $J_{F3}$ from the solution by adding anti-solvent selected from alkyl esters.

In accordance with another embodiment, the polymorphic form $J_{F3}$ is prepared by dissolving Fluvastatin sodium in methanol, followed by addition of anti-solvent selected from alkyl esters.

In accordance with another embodiment, there is provided a process for preparing Fluvastatin sodium in amorphous form, wherein the process comprising dissolving Fluvastatin lower alkyl ester in methanol, adding sodium hydroxide to the solution and isolating Fluvastatin sodium in amorphous form from the solution by optionally adding anti-solvent selected from hydrocarbon.

Further embodiment of the present invention provides a process for preparing amorphous form of Fluvastatin, wherein said process comprising dissolving Fluvastatin sodium in methanol, and then isolating Fluvastatin sodium in amorphous form from the solution by optionally adding anti-solvent selected from hydrocarbon.

The novel polymorphic forms of Fluvastatin sodium described herein-in the present invention can be effectively used as pharmaceutical agents.

BRIEF DESCRIPTION OF THE DRAWING FIGURES

Further objects of the present invention together with additional features contributing thereto and advantages accruing there from will be apparent from the description of preferred embodiments of the present invention which are shown in the accompanying drawing figures.

Figure 3:
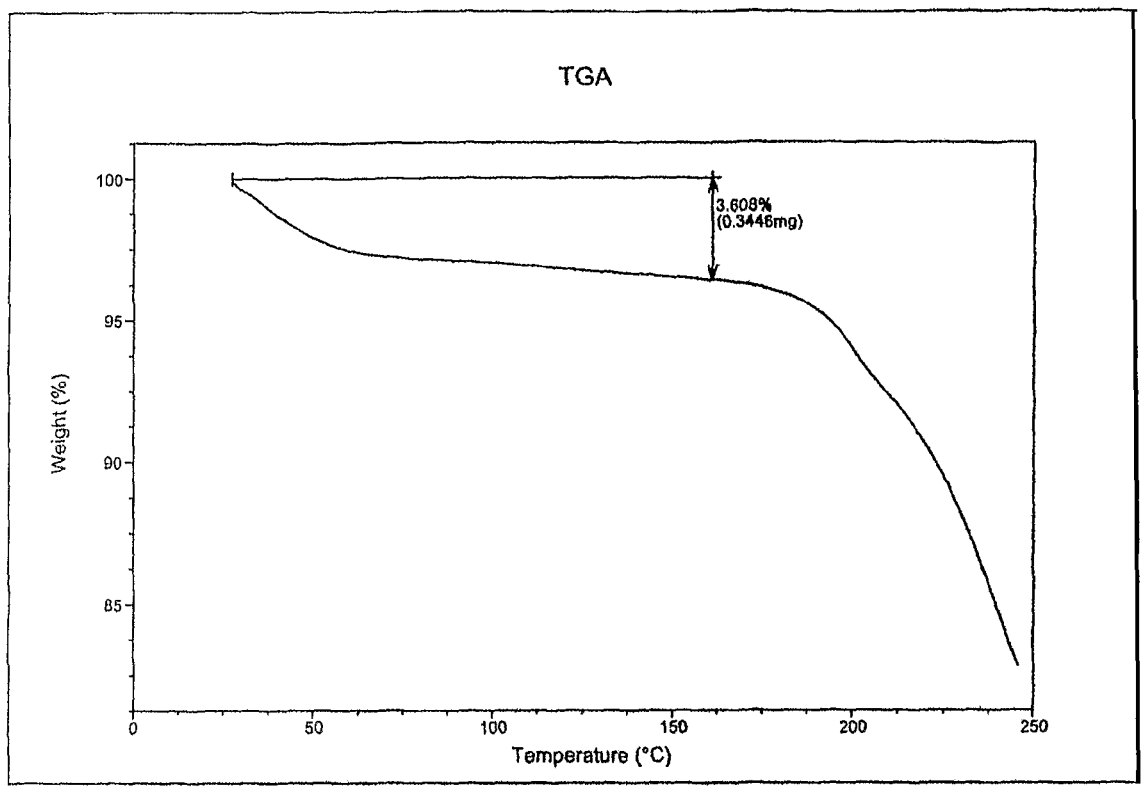
Figure 4:
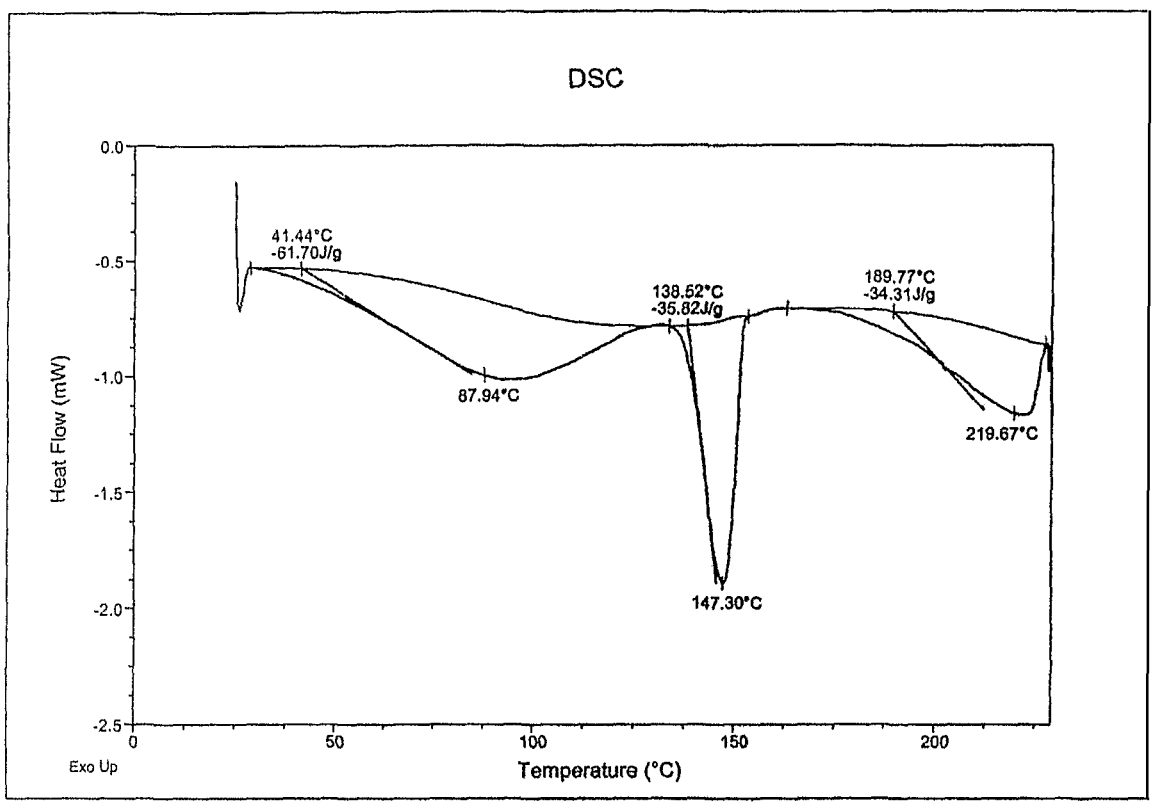
Figure 7:
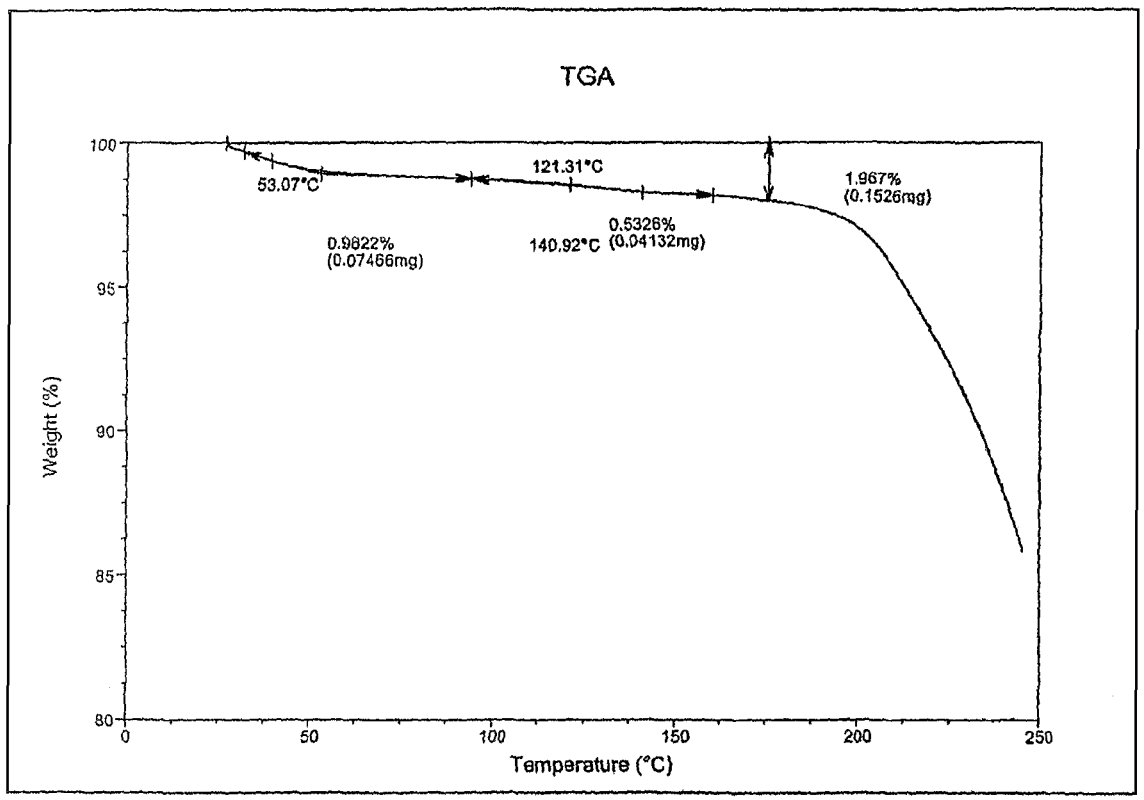
Figure 8:
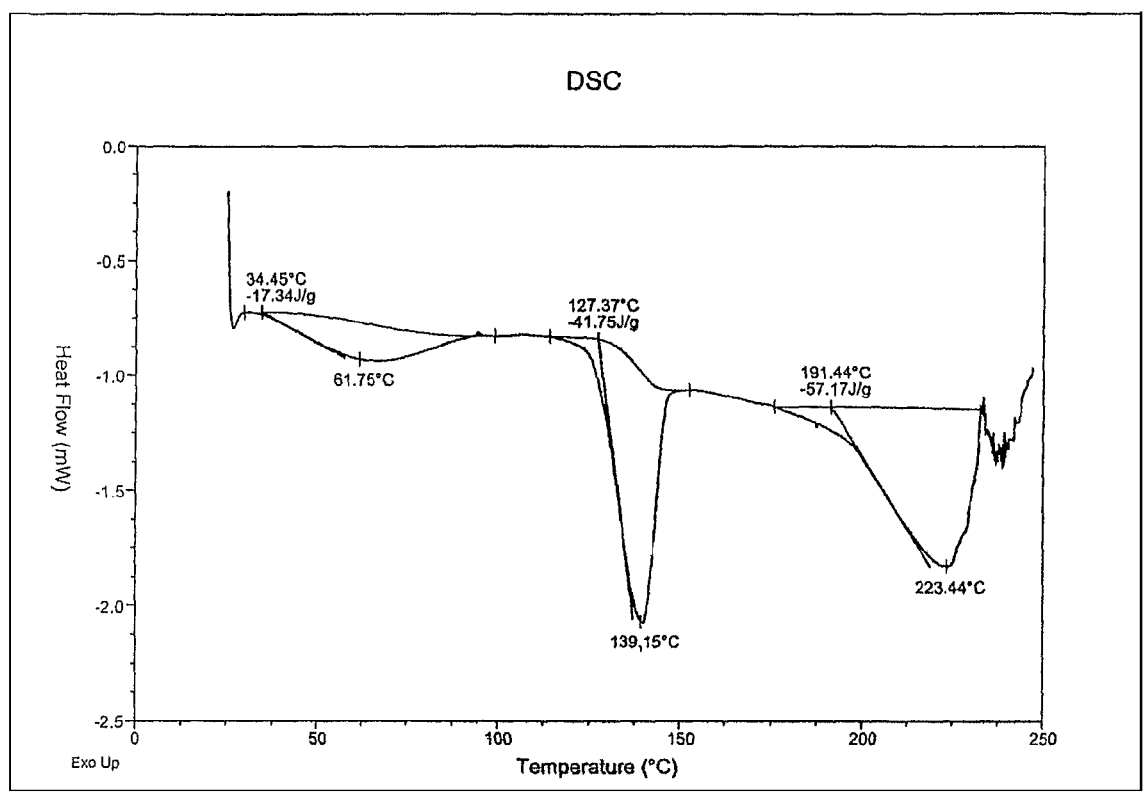
Figure 11:
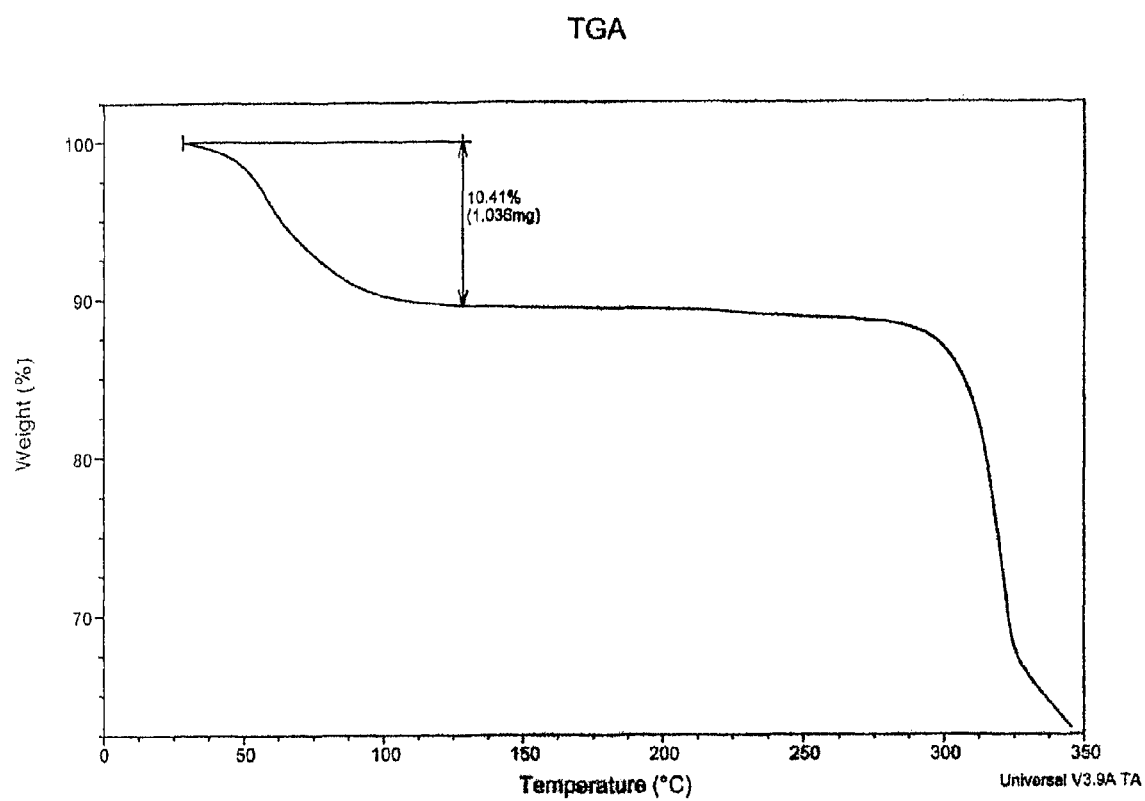
Figure 12:
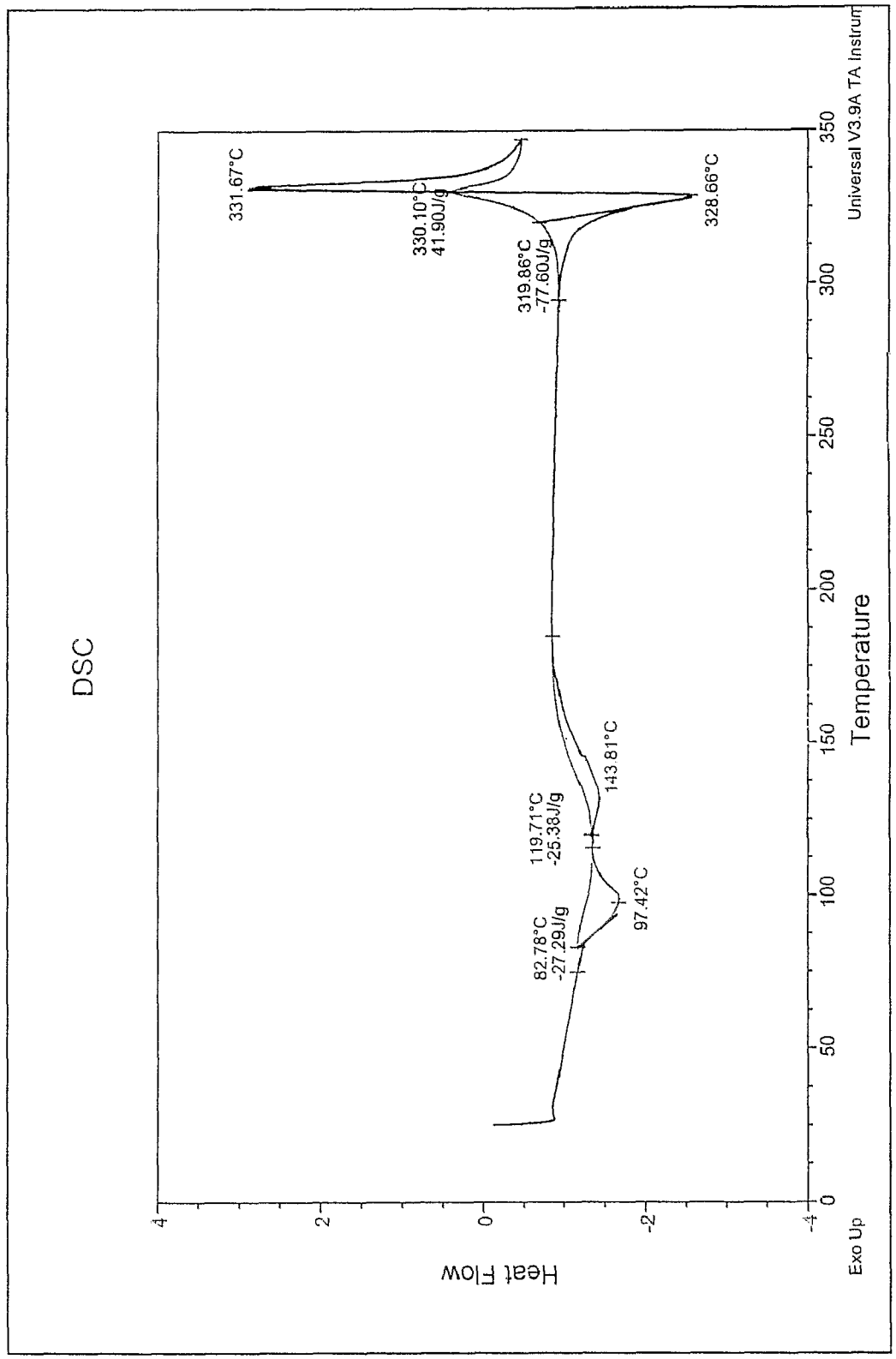
Figure 15:
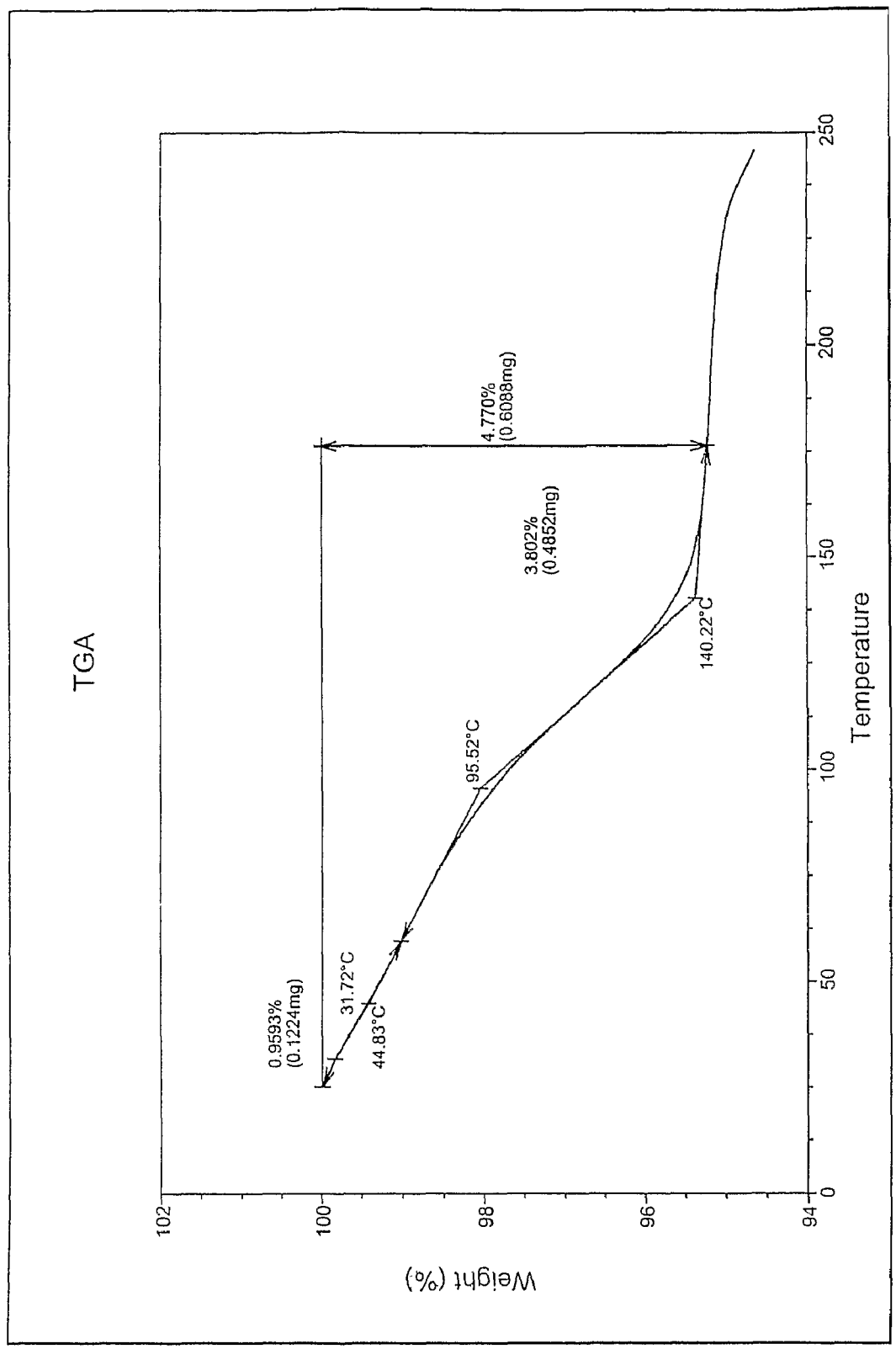
Figure 16:
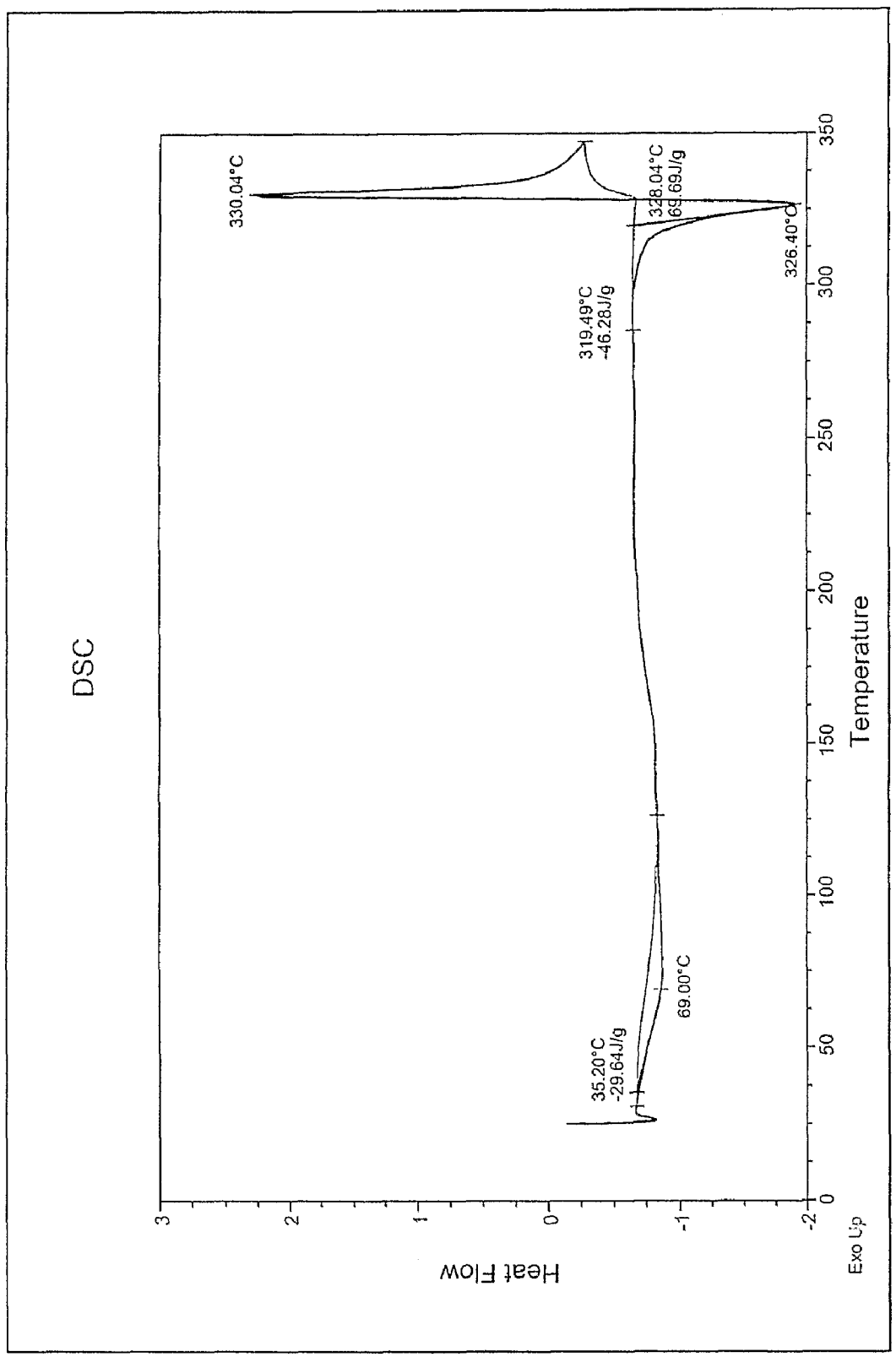
Figure 17:
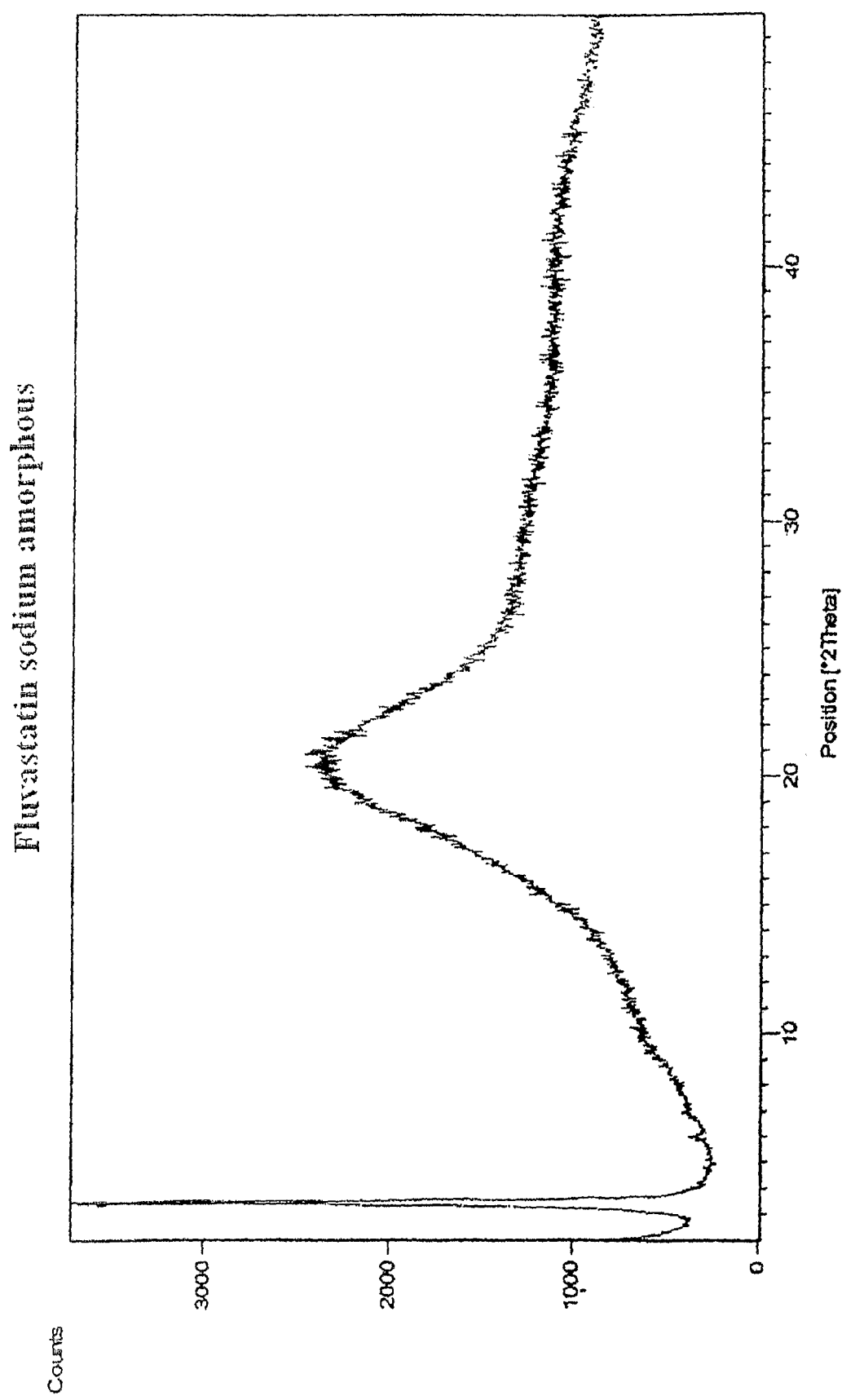

FIG. 1 depicts a powder X-ray diffractogram of crystalline Fluvastatin sodium, Form $J_F$ FIG. 2 depicts infrared absorption spectrum of crystalline Fluvastatin sodium Form $J_F$ FIG. 3 depicts Thermo gravimetric analysis of crystalline Fluvastatin sodium Form $J_F$ FIG. 4 depicts Differential scanning calorimetry of Fluvastatin sodium Form $J_F$ FIG. 5 depicts a powder X-ray diffractogram of crystalline Fluvastatin sodium, Form $J_{F1}$ FIG. 6 depicts infrared absorption spectrum of crystalline Fluvastatin sodium Form $J_{F1}$ FIG. 7 depicts Thermo gravimetric analysis of crystalline Fluvastatin sodium Form $J_{F1}$ FIG. 8 depicts Differential scanning calorimetry of Fluvastatin sodium Form $J_{F1}$ FIG. 9 depicts a powder X-ray diffractogram of crystalline Fluvastatin sodium, Form $J_{F2}$ FIG. 10 depicts infrared absorption spectrum of crystalline Fluvastatin sodium Form $J_{F2}$ FIG. 11 depicts Thermo gravimetric analysis of crystalline Fluvastatin sodium Form $J_{F2}$ FIG. 12 depicts Differential scanning calorimetry of Fluvastatin sodium Form $J_{F2}$ FIG. 13 depicts a powder X-ray diffractogram of crystalline Fluvastatin sodium, Form $J_{F3}$ FIG. 14 depicts infrared absorption spectrum of crystalline Fluvastatin sodium Form $J_{F3}$ FIG. 15 depicts Thermo gravimetric analysis of crystalline Fluvastatin sodium Form $J_{F3}$ FIG. 16 depicts Differential scanning calorimetry of Fluvastatin sodium Form $J_{F3}$ FIG. 17 depicts a powder X-ray diffractogram of amorphous Fluvastatin sodium

DESCRIPTION OF THE INVENTION

While this specification concludes with claims particularly pointing out and distinctly claiming that, which is regarded as the invention, it is anticipated that the invention can be more readily understood through reading the following detailed description of the invention and study of the included drawings.

The present invention discloses in its aspect novel crystalline polymorphic forms of Fluvastatin sodium designated as Form $J_F$, $J_{F1}$, $J_{F2}$ and $J_{F3}$ that may also exist in solvate forms and are intended to be encompassed within the scope of the present invention. The present invention also provides process for the preparation of Fluvastatin sodium in amorphous form.

Fluvastatin sodium Forms $J_F$, $J_{F1}$, $J_{F2}$, $J_{F3}$ and amorphous forms differ from each other in their physical properties, spectral data and process of preparation and are characterized by their X-ray powder diffraction patterns, infra red absorption spectra, differential scanning calorimetry and/or by their thermo gravimetric analysis (TGA).

X-ray Powder Diffraction

Crystalline Fluvastatin sodium Forms $J_F$, $J_{F1}$, $J_{F2}$, $J_{F3}$ and amorphous forms are characterized by their X-ray powder diffraction pattern. Thus the X-ray diffraction patterns of crystalline Fluvastatin sodium Forms are measured on a PANalytical X' Pert Pro diffractometer with Cu radiation and expressed in terms of 2θ, d-spacing and relative intensities.

Methodology

Continuous θ/2θ coupled scan 2.0° to 50° in 2θ, scan speed of 0.05°/sec.

Infrared absorption spectrometer (IR)

Methodology

All infrared measurement were made on Thermo Nicolet FT IR spectrometer using KBr pellets having the characteristic absorption bands expressed in reciprocal centimeter.

Thermo Gravimetric Analysis (TGA)

Methodology

TGA thermogram is recorded on TGA Q 50 with a ramp of 10° C./min to 350° C. with nitrogen flow rate 60 ml/minute.

Differential Scanning Calorimetry (DSC)

Methodology

DSC thermogram is recorded on DSCQ100 equilibrated at 25° C. to 350° C. at 10° C./minute with nitrogen flow rate 60 ml/minute.

Crystalline Fluvastatin sodium Form $J_F$ is characterized by powder X-ray diffraction pattern having peaks at 3.3, 3.9, 10.0, 10.9, 17.1, 19.3, 20.6±0.2°2θ as depicted in FIG. 1.

Crystalline Fluvastatin sodium Form $J_F$ is further characterized by having an infrared spectrum in KBr comprising one or more characteristic peaks selected from absorption bands (cm$^{-1}$) 3399(s), 2973(m), 2934(m), 1577(s), 1536(w), 1500 (s), 1455(w), 1418(w), 1370(w), 1342(m), 1217(s), 1154(s), 1106(m), 1068(w), 1019(w), 974(m), 941(w), 839(s), 813 (m), 741(s), 717(w), 688(w), 654(m), 564(s), 522(m); wherein (w)=weak intensity; (m)=medium intensity; (s)=strong intensity as depicted in FIG. 2.

Crystalline Fluvastatin sodium Form $J_F$ is prepared by hydrolyzing Fluvastatin lower alkyl ester selected from $C_{1-4}$ alkyl ester in methanol, adding sodium hydroxide solution taken in water and cooled to 0-10° C., preferably 0-5° C. The resulting reaction mixture is stirred at room temperature for 1-3 hours. Solvent is distilled off. The resulting mass is dissolved in an organic solvent such as methanol, heated to about 30-60° C., preferably 40-50° C. to obtain clear solution. Water can be added optionally. The moisture content of the resulting solution is maintained between 3-8% by volume preferably between 4-6% by volume. Anti-solvent, selected from lower alkyl alcohol such as ethanol, propanol or mixture thereof, is added. The resulting solution is seeded with Fluvastatin sodium Form $J_F$ and stirred at room temperature for 15-20 hours, preferably 16-18 hours. The solid is then separated out from the solvent by, for example, filtering or decanting under an inert atmosphere and dried under vacuum at 50-60° C. for 30-60 hours preferably 35-45 hours.

Crystalline Fluvastatin sodium Form $J_F$ can also be prepared by dissolving Fluvastatin sodium in methanol and heating to about 30-60° C., more preferably 40-50° C. to obtain clear solution. Water can be added optionally. The moisture content of the resulting solution is maintained between 3-8% by volume preferably between 4-6% by volume. Anti-solvent, selected from lower alkyl alcohol such as ethanol, propanol or mixture thereof, is added. The resulting solution is seeded with Fluvastatin sodium Form $J_F$ and stirred at room temperature for 15-20 hours, preferably 16-18 hours. The solid is then separated out from the solvent by, for example, filtering or decanting under an inert atmosphere and drying under vacuum at 50-60° C. for 30-60 hours, preferably 35-45 hours.

Crystalline Fluvastatin sodium Form $J_{F1}$ is characterized by powder X-ray diffraction pattern with peaks at 3.7, 4.9, 5.5, 9.8, 10.2, 11.2, 12.1±0.2°2θ as shown in FIG. 5.

Crystalline Fluvastatin sodium Form $J_{F1}$ is further characterized by having an infrared spectrum in KBr comprising one or more characteristic peaks selected from absorption bands (cm$^{-1}$) 3392(s), 2975(m), 2935(m), 2867(w), 1575(s), 1533 (w), 1499(s), 1455(w), 1412(w), 1401(w), 1371(w), 1344 (m), 1215(s), 1155(s), 1106(m), 1068(w), 1020(w), 972(m), 941(w), 887(w), 839(s), 813(s), 740(s), 718(w), 690(w), 653 (m), 564(s), 522(m); wherein (w)=weak intensity; (m)=medium intensity; (s)=strong intensity as depicted in FIG. 6.

Crystalline Fluvastatin sodium Form $J_{F1}$ is prepared by hydrolyzing Fluvastatin lower alkyl ester selected from $C_{1-4}$ alkyl ester in methanol, adding sodium hydroxide solution taken in water and cooled to 0-10° C., preferably 0-5° C. The resulting reaction mixture is stirred at room temperature for 1-3 hours. Solvent is distilled off. The resulting mass is dissolved in an organic solvent such as methanol, heated to about 30-60° C., preferably about 40-50° C. to obtain clear solution. Water can be added optionally. The moisture content of the resulting solution is maintained between 3-8% by volume preferably between 4-6% by volume. Anti-solvent, selected from nitrites, preferably acetonitrile, propionitrile or mixture thereof, is added. The resulting solution is seeded with Fluvastatin sodium Form $J_{F1}$ and stirred at room temperature for 15-20 hours, preferably 16-18 hours. The solid is then separated out from the solvent by, for example, filtering or decanting under an inert atmosphere and dried under vacuum at 50-60° C. for 30-60 hours preferably 35-40 hours.

Crystalline Fluvastatin sodium Form $J_{F1}$ can also be prepared by dissolving Fluvastatin sodium in methanol, heating to about 30-60° C., preferably about 40-50° C. to obtain clear solution. Water can be added optionally. The moisture content of the resulting solution is maintained between 3-8% by volume preferably between 4-6% by volume. Anti-solvent, selected from nitrites, preferably acetonitrile, propionitrile or mixture thereof, is added. The resulting solution is seeded with Fluvastatin sodium Form $J_{F1}$ and stirred at room temperature for 15-20 hours, preferably 16-18 hours. The solid is then separated out from the solvent by, for example, filtering or decanting under an inert atmosphere and drying under vacuum at 50-60° C. for 30-60 hours, preferably 35-40 hours.

Crystalline Fluvastatin sodium Form $J_{F2}$ is characterized by powder X-ray diffraction pattern characterized by a PXRD pattern with peaks at 4.9, 5.2, 5.6, 10.2, 10.8, 11.6, 17.6, 20.9±0.2°2θ as shown in FIG. 9.

Crystalline Fluvastatin sodium Form $J_{F2}$ is further characterized by having an infrared spectrum in KBr comprising one or more characteristic peaks selected from absorption bands ($cm^{-1}$) 3403(s), 2976(m), 2935(m), 2902(w), 1722(m), 1618 (w), 1572(s), 1500(s), 1457(s), 1402(s), 1370(w), 1344(m), 1219(s), 1155(s), 1104(s), 969(s), 928(w), 837(s), 814(m), 741(s), 718(w), 695(w), 653(w), 565(s), 522(m); wherein (w)=weak intensity; (m)=medium intensity; (s)=strong intensity as depicted in FIG. 10.

Crystalline Fluvastatin sodium Form $J_{F2}$, is prepared by hydrolyzing Fluvastatin lower alkyl ester selected from $C_{1-4}$ alkyl ester in methanol, adding sodium hydroxide solution taken in water and cooled to 0-10° C. preferably 0-5° C. The resulting reaction mixture is stirred at room temperature for 1-3 hours. Solvent is distilled off. The resulting mass is dissolved in an organic solvent such as methanol, heated to about, heated to about 30-60° C., preferably 40-50° C. to obtain clear solution. Water can be added optionally. The moisture content of the resulting solution is maintained between 0.5-4% preferably between 1-2%. Anti-solvent selected from alkyl esters preferably ethyl acetate, butyl acetate or mixture thereof, is added. The resulting solution is seeded with Fluvastatin sodium Form $J_{F2}$ and stirred at room temperature for 15-20 hours, preferably 16-18 hours. The solid is then separated out from the solvent by, for example, filtering or decanting under an inert atmosphere and air-dried for 30-60 minutes.

Crystalline Fluvastatin sodium Form $J_{F2}$ can also be prepared by dissolving Fluvastatin sodium in methanol, heating to about heated to about 30-60° C., preferably 40-50° C. to obtain clear solution. Water can be added optionally. The moisture content of the resulting solution is maintained between 0.5-4% preferably between 1-2%. Anti-solvent selected from alkyl esters preferably ethyl acetate, butyl acetate or mixture thereof, is added. The resulting solution is seeded with Fluvastatin sodium Form $J_{F2}$ and stirred at room temperature for 15-20 hours, preferably 16-18 hours. The solid is then separated out from the solvent by, for example, filtering or decanting under an inert atmosphere and then air-dried for 30-60 minutes.

Crystalline Fluvastatin sodium Form $J_{F3}$ is characterized by powder X-ray diffraction pattern characterized by a PXRD pattern with peaks at 5.2, 5.5, 6.0, 10.2±0.2°2θ as shown in FIG. 13.

Crystalline Fluvastatin sodium Form $J_{F3}$ is further characterized by having an infrared spectrum in KBr comprising one or more characteristic peaks selected from absorption bands ($cm^{-1}$) 3411(s), 2974(m), 2935(w), 1673(w), 1617(w), 1561 (s), 1500(s), 1457(s), 1403(s), 1369(w), 1343(m), 1220(s), 1155(m), 1104(s), 1063(w), 1014(w), 974(m), 837(s), 815 (m), 742(s), 715(w), 696(w), 654(w), 565(s), 519(m); wherein (w)=weak intensity; (m)=medium intensity; (s)=strong intensity as depicted in FIG. 14.

Crystalline Fluvastatin sodium Form $J_{F3}$, is prepared by hydrolyzing Fluvastatin lower alkyl ester selected from $C_{1-4}$ alkyl ester in methanol, adding sodium hydroxide solution taken in water and cooled to 0-10° C. preferably 0-5° C. The resulting reaction mixture is stirred at room temperature for 1-3 hours. Solvent is distilled off. The resulting mass is dissolved in methanol, heated to about heated to about 30-60° C., preferably 40-50° C. to obtain clear solution. Water can be added optionally. The moisture content of the resulting solution is maintained between 0.5-4% preferably between 1-2%. Anti-solvent, selected from alkyl esters preferably ethyl acetate, butyl acetate or mixture thereof, is added. The resulting solution is seeded with Fluvastatin sodium Form $J_{F3}$ and stirred at room temperature for 15-20 hours, preferably 16-18 hours. The solid is then separated out from the solvent by, for example, filtering or decanting under an inert atmosphere and dried under vacuum at 50-60° C. for 30-60 hours, preferably 35-40 hours.

Crystalline Fluvastatin sodium Form $J_{F3}$ can also be prepared by dissolving Fluvastatin sodium in methanol, heated to about heated to about 30-60° C., preferably 40-50° C. to obtain clear solution. Water can be added optionally. The moisture content of the resulting solution is maintained between 0.5-4% preferably between 1-2%. Anti-solvent, selected from alkyl esters preferably ethyl acetate, butyl acetate or mixture thereof, is added. The resulting solution is seeded with Fluvastatin sodium Form $J_{F3}$ and stirred at room temperature for 15-20 hours, preferably 16-18 hours. The solid is then separated out from the solvent by, for example, filtering or decanting under an inert atmosphere and dried under vacuum at 50-60° C. for 30-60 hours preferably 35-40 hours.

Disclosed herein according to the present invention, Fluvastatin sodium in amorphous form, is prepared by dissolving Fluvastatin lower alkyl ester selected from $C_{1-4}$ alkyl ester in methanol, adding sodium hydroxide solution taken in water and cooled to 0-10° C. preferably 0-5° C. The resulting reaction mixture is stirred at room temperature for 1-3 hours. Solvent was distilled off. The resulting mass is dissolved in methanol, heated to about 45-60° C. to obtain clear solution. Methanol was distilled off. Anti-solvent, selected from hydrocarbon preferably n-hexane, n-heptane, n-octane or mixture thereof, is added and was stirred for 1-2 hours preferably 30-50 minutes. The solid is then separated out from the solvent by, for example, filtering or decanting under an inert atmosphere and dried under vacuum at 65-75° C. for 30-60 hours preferably 35-40 hours.

Fluvastatin sodium in amorphous form can also be prepared by dissolving Fluvastatin sodium in methanol, heated to about 45-60° C. to obtain clear solution. Solvent was distilled off. Anti-solvent, selected from hydrocarbon preferably n-hexane, n-heptane, n-octane or mixture thereof, is added and was stirred for 1-2 hours preferably 30-50 minutes. The solid is then separated out from the solvent by, for example, filtering or decanting under an inert atmosphere and dried under vacuum at 65-75° C. for 30-60 hours preferably 35-40 hours.

The following non-limiting examples illustrate specific embodiments of the present invention. They are, however, not intended to be limiting the scope of present invention in any way.

EXAMPLE 1

Preparation of Crystalline Fluvastatin sodium Form $J_F$

Fluvastatin ethyl ester (30 gm) was taken in methanol (180 ml) and cooled to 2-5° C. Sodium hydroxide taken in water was added at above temperature. The reaction mixture was stirred at 25-30° C. for 90-120 minutes. The resulting mixture was treated with activated carbon and filtered. Solvent was distilled off. To the resulting residue, methanol (60 ml) was added and stirred at 45-50° C. to obtain clear solution. Water was added optionally. Absolute alcohol (180 ml) was added. The resulting solution was seeded with Fluvastatin sodium Form $J_F$ and stirred at 25-30° C. for 15-20 hours. The resulting solid was filtered off under inert atmosphere, washed with chilled absolute alcohol and dried under vacuum at 50-60° C. for 30-50 hours.

EXAMPLE 2

Preparation of Crystalline Fluvastatin sodium Form $J_F$

Fluvastatin sodium (30 gm) was taken in methanol (60 ml) and stirred at 45-50° C. to obtain clear solution. Water was added optionally. Absolute alcohol (180 ml) was added. The resulting solution was seeded with Fluvastatin sodium Form $J_F$ and stirred at 25-30° C. for 15-20 hours. The resulting solid was filtered off under inert atmosphere, washed with chilled absolute alcohol and dried under vacuum at 50-60° C. for 30-45 hours.

EXAMPLE 3

Preparation of Crystalline Fluvastatin sodium Form $J_{F1}$

Fluvastatin ethyl ester (30 gm) was taken in methanol (180 ml) and cooled to 2-5° C. Sodium hydroxide solution was added at above temperature. The reaction mixture was stirred at 25-30° C. for 90-120 minutes. The resulting mixture was treated with activated carbon and filtered. Solvent was distilled off. To the resulting residue, methanol (60 ml) was added and stirred at 45-50° C. to obtain clear solution. Water was added optionally. Acetonitrile (180 ml) was added and the resulting solution was seeded with Fluvastatin sodium Form $J_{F1}$ and stirred at 25-30° C. for 15-18 hours. The resulting solid was filtered off under inert atmosphere, washed with chilled acetonitrile and dried under vacuum at 50-60° C. for 30-40 hours.

EXAMPLE 4

Preparation of Crystalline Fluvastatin sodium Form $J_{F1}$

Fluvastatin sodium (30 gm) was taken in methanol (60 ml) and stirred at 45-50° C. to obtain clear solution. Water was added optionally. Acetonitrile (180 ml) was added and the resulting solution was seeded with Fluvastatin sodium Form $J_{F1}$ and stirred at 25-30° C. for 15-18 hours. The resulting solid was filtered off under inert atmosphere, washed with chilled acetonitrile and dried under vacuum at 50-60° C. for 30-45 hours.

EXAMPLE 5

Preparation of Crystalline Fluvastatin sodium Form $J_{F2}$

Fluvastatin ethyl ester (30 gm) was taken in methanol (180 ml) and cooled to 2-5° C. Sodium hydroxide solution was added at 2-5° C. The reaction mixture was stirred at 25-30° C. for 90-120 minutes. The resulting mixture was treated with activated carbon and filtered. Solvent was distilled off. To the resulting residue, methanol (60 ml) was added and stirred at 45-50° C. to obtain clear solution. Water was added optionally. Ethyl acetate (160 ml) was added and the resulting solution was seeded with Fluvastatin sodium Form $J_{F2}$ and stirred at 25-30° C. for 15-18 hours. The resulting solid was filtered off under inert atmosphere, washed with chilled ethyl acetate and air-dried for 30-60 minutes.

EXAMPLE 6

Preparation of Crystalline Fluvastatin sodium Form $J_{F2}$

Fluvastatin sodium (30 gm) was taken in methanol (60 ml) and stirred at 45-50° C. to obtain clear solution. Water was added optionally. Ethyl acetate (160 ml) was added and the resulting solution was seeded with Fluvastatin sodium Form $J_{F2}$ and stirred at 25-30° C. for 15-18 hours. The resulting solid was filtered off under inert atmosphere, washed with chilled ethyl acetate and air-dried for 30-60 minutes.

EXAMPLE 7

Preparation of Crystalline Fluvastatin sodium Form $J_{F3}$

Fluvastatin ethyl ester (30 gm) was taken in methanol (180 ml) and cooled to 5° C. Sodium hydroxide solution was added at 2-5° C. The reaction mixture was stirred at 25-30° C. for 90-120 minutes. The resulting mixture was treated with activated carbon and filtered. Solvent was distilled off. To the resulting residue, methanol (60 ml) was added and stirred at 45-50° C. to obtain clear solution. Water was added optionally. Ethyl acetate (160 ml) was added and the resulting solution was seeded with Fluvastatin sodium Form $J_{F3}$ and stirred at 25-30° C. for 15-18 hours. The resulting solid was filtered off under inert atmosphere, washed with chilled ethyl acetate and dried under vacuum at 50-60° C. for 30-40 hours.

EXAMPLE 8

Preparation of Crystalline Fluvastatin sodium Form $J_{F3}$

Fluvastatin sodium (30 gm) was taken in methanol (60 ml) and stirred at 45-50° C. to obtain clear solution. Water was added optionally. Ethyl acetate (160 ml) was added and the resulting solution was seeded with Fluvastatin sodium Form $J_{F3}$ and stirred at 25-30° C. for 15-18 hours. The resulting solid was filtered off under inert atmosphere, washed with chilled ethyl acetate and dried under vacuum at 50-60° C. for 30-40 hours.

EXAMPLE 9

Preparation of Amorphous Fluvastatin Sodium

Fluvastatin ethyl ester (30 gm) was taken in methanol (180 ml) and cooled to 5° C. Sodium hydroxide solution was added at 5-10° C. The reaction mixture was stirred at 25-30° C. for 90-120 minutes. The resulting mixture was treated with activated carbon and filtered. Solvent was distilled off. To the resulting residue, methanol (150 ml) was added and stirs at 45-50° C. to obtain clear solution. Methanol was distilled off completely and n-heptane (150 ml) was added, stir for 30-40 minutes. The resulting solid was filtered off under inert atmosphere, washed with n-heptane and dried under vacuum at 65-75° C. for 30-40 hours.

EXAMPLE 10

Preparation of Amorphous Fluvastatin Sodium

Fluvastatin sodium (30 gm) was taken in methanol (150 ml) and stir at 45-50° C. to obtain clear solution. Methanol was distilled off completely, n-heptane (150 ml) was added and stir for 30-40 minutes. The resulting solid was filtered off under inert atmosphere, washed with n-heptane and dried under vacuum at 65-75° C. for 30-40 hours.

While this invention has been described in detail with reference to certain preferred embodiments, it should be appreciated that the present invention is not limited to those precise embodiments. Rather, in view of the present disclosure, which describes the current best mode for practicing the invention, many modifications and variations would present themselves to those skilled in the art without departing from the scope and spirit of this invention.

We claim:

1. A process for the preparation of amorphous form of Fluvastatin sodium comprising:
    (a) hydrolyzing a lower alkyl ester of Fluvastatin in a solution containing sodium hydroxide in a mixture consisting of methanol,
    (b) evaporating the methanol from the mixture to obtain residue,
    (c) dissolving the residue in methanol,
    (d) removing the methanol to obtain the solid, and
    (e) optionally adding anti-solvent to isolate amorphous Fluvastatin sodium.

2. The process according to claim 1, wherein the anti-solvent is selected from n-hexane, n-heptane or n-octane or mixture thereof.

3. A process for the preparation of amorphous form of Fluvastatin sodium comprising:
    (a) dissolving Fluvastatin sodium in methanol,
    (b) removing the methanol to obtain the solid, and
    (c) optionally adding anti-solvent to isolate amorphous Fluvastatin sodium.

4. The process according to claim 3, wherein the anti-solvent is selected from n-hexane, n-heptane or n-octane or mixture thereof.

5. The process according to claim 2, comprising adding the anti-solvent to isolate amorphous Fluvastatin sodium.

6. The process according to claim 1, comprising adding the anti-solvent to isolate amorphous Fluvastatin sodium.

7. The process according to claim 1, wherein the amorphous Fluvastatin sodium has a powder X-ray diffractogram substantially as in FIG. 17.

8. The process according to claim 1, further comprising cooling the composition of step (a) to about 0-10 degrees C.

9. The process according to claim 8, further comprising stifling the composition of step (a) at room temperature after being cooled.

10. The process according to claim 9, wherein the stirring is for about 1-3 hours.

11. The process according to claim 1, further comprising heating the composition of step (c) to about 45-60 degrees C.

12. The process according to claim 1, further comprising heating the composition of step (c) until a clear solution is obtained.

13. The process according to claim 5, further comprising stifling the composition of anti-solvent and Fluvastatin sodium for at least 30 minutes.

14. The process according to claim 5, further comprising filtering or decanting the composition of anti-solvent and Fluvastatin sodium under inert atmosphere to obtain a solid.

15. The process according to claim 14, further comprising drying the filtered or decanted solid.

16. The process according to claim 15, wherein the drying is at about 65-75 degrees C. and/or for about 30-60 hours.

17. The process according to claim 3, wherein the amorphous Fluvastatin sodium has a powder X-ray diffractogram substantially as in FIG. 17.

18. The process according to claim 3, further comprising heating the composition of step (a) to about 45-60 degrees C.

19. The process according to claim 3, further comprising heating the composition of step (a) until a clear solution is obtained.

20. The process according to claim 19, further comprising filtering or decanting the composition of anti-solvent and Fluvastatin sodium under inert atmosphere to obtain a solid.

* * * * *